US009248197B2

(12) United States Patent
Lees

(10) Patent No.: US 9,248,197 B2
(45) Date of Patent: *Feb. 2, 2016

(54) ACTIVATION OF POLYSACCHARIDES VIA THE CYANYLATING AGENT, 1-CYANOIMIDAZOLE (1-CI), IN THE PREPARATION OF POLYSACCHARIDE/PROTEIN CONJUGATE VACCINES

(71) Applicant: Fina Biosolutions, LLC, Rockville, MD (US)

(72) Inventor: Andrew Lees, Silver Spring, MD (US)

(73) Assignee: Fina BioSolutions, LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/312,748

(22) Filed: Jun. 24, 2014

(65) Prior Publication Data

US 2014/0316110 A1 Oct. 23, 2014

Related U.S. Application Data

(63) Continuation of application No. 13/514,356, filed as application No. PCT/US2010/061133 on Dec. 17, 2010, now Pat. No. 9,044,517.

(60) Provisional application No. 61/287,593, filed on Dec. 17, 2009.

(51) Int. Cl.
| | |
|---|---|
| A61K 47/48 | (2006.01) |
| C08B 37/02 | (2006.01) |
| C08B 37/00 | (2006.01) |
| C08H 1/00 | (2006.01) |
| A61K 39/095 | (2006.01) |
| A61K 39/145 | (2006.01) |
| A61K 39/00 | (2006.01) |

(52) U.S. Cl.
CPC ............ *A61K 47/4823* (2013.01); *A61K 39/00* (2013.01); *A61K 39/095* (2013.01); *A61K 39/145* (2013.01); *A61K 47/48284* (2013.01); *C08B 37/006* (2013.01); *C08B 37/0021* (2013.01); *C08H 1/00* (2013.01); *A61K 2039/6087* (2013.01); *A61K 2039/627* (2013.01)

(58) Field of Classification Search
None
See application file for complete search history.

(56) References Cited

U.S. PATENT DOCUMENTS

| | | | |
|---|---|---|---|
| 4,356,170 A | 10/1982 | Jennings et al. | |
| 4,540,573 A | 9/1985 | Neurath et al. | |
| 4,663,160 A | 5/1987 | Tsay et al. | |
| 4,678,553 A | 7/1987 | Mandle et al. | |
| 4,695,624 A | 9/1987 | Marburg et al. | |
| 5,039,607 A | 8/1991 | Skold et al. | |
| 5,306,492 A | 4/1994 | Porro | |
| 5,360,897 A | 11/1994 | Anderson et al. | |
| 5,425,946 A | 6/1995 | Tai et al. | |
| 5,585,100 A | 12/1996 | Mond et al. | |
| 5,651,971 A | 7/1997 | Lees | |
| 5,693,326 A | 12/1997 | Lees | |
| 5,747,663 A | 5/1998 | Colpan et al. | |
| 5,849,301 A | 12/1998 | Lees | |
| 5,955,079 A | 9/1999 | Mond et al. | |
| 6,087,328 A | 7/2000 | Lees | |
| 6,146,902 A | 11/2000 | McMaster | |
| 6,248,334 B1 | 6/2001 | Lees et al. | |
| 6,284,250 B1 | 9/2001 | Lees et al. | |
| 6,299,881 B1 | 10/2001 | Lees et al. | |
| 6,309,646 B1 | 10/2001 | Lees | |
| 6,428,703 B1 | 8/2002 | Zinn et al. | |
| 6,432,679 B1 | 8/2002 | Mond et al. | |
| 6,585,973 B1 | 7/2003 | Lees | |
| 6,596,172 B1 | 7/2003 | Kopf | |
| 6,756,041 B2 | 6/2004 | Lees et al. | |
| 6,765,091 B1 | 7/2004 | Bencomo et al. | |
| 7,094,883 B1 | 8/2006 | Cassels et al. | |
| 7,101,562 B1 | 9/2006 | Lees et al. | |
| 7,166,708 B2 | 1/2007 | Lees et al. | |
| 7,250,494 B2 | 7/2007 | Stinson et al. | |
| 7,452,533 B2 | 11/2008 | Walsh et al. | |
| 7,470,441 B2 | 12/2008 | Van Der Giessen et al. | |
| 7,566,540 B2 | 7/2009 | Cassels et al. | |
| 7,777,017 B2 | 8/2010 | Stinson et al. | |
| 2002/0054879 A1 | 5/2002 | Lees et al. | |

(Continued)

FOREIGN PATENT DOCUMENTS

| | | |
|---|---|---|
| EP | 1163000 | 2/2008 |
| JP | 2004501869 | 1/2004 |

(Continued)

OTHER PUBLICATIONS

Canada Office Action for PCT/US10/61133, dated Jan. 9, 2015.
Suárez, et al, "Improved conjugation and purification strategies for the preparation of protein-polysaccharide conjugates," J. Chromatogr A, 1213, pp. 169-175, 2008.
Bystrický, et al, "Candida albicans mannan-protein conjugate as vaccine candidate," Immunol Lett., 85, pp. 251-255, 2003.
Wu, et al, "1-Cyanoimidazole as a mild and efficient electrophilic cyanating agents," J Org Lett, pp. 795-797, 2000.
Mexico Office Action for PCT/US10/61133, dated Nov. 18, 2014.
R. Wong & H, Tse, Lateral Flow Immunoassay, Humana Press (2009).
Bioconjugate Protocols: Strategies and Methods (Methods in Moldecular Biology) Christof M. Niemeyer (Editor) Humana Press (2009).

(Continued)

Primary Examiner — Eric Olson
Assistant Examiner — Dale R Miller
(74) Attorney, Agent, or Firm — Remenick PLLC

(57) ABSTRACT

This invention provides novel reagents for cyanating polysaccharides in aqueous or part aqueous solutions so that they may be covalently linked to proteins either directly or through a spacer. These reagents include 1-cyano-4-pyrrolidinopyridinium tetrafluoroborate (CPPT), 1-cyano-imidazole (1-CI), 1-cyanobenzotriazole (1-CBT), or 2-cyanopyridazine-3(2H) one (2-CPO), or a functional derivative or modification thereof. The examples illustrate the use of these reagents with a variety of polysaccharides and proteins showing that the methods are generally applicable.

8 Claims, 5 Drawing Sheets

(56) References Cited

U.S. PATENT DOCUMENTS

| | | | |
|---|---|---|---|
| 2002/0119529 | A1 | 8/2002 | Mond et al. |
| 2003/0215436 | A1 | 11/2003 | Walsh et al. |
| 2003/0224000 | A1 | 12/2003 | Kokai-Kun et al. |
| 2003/0235578 | A1 | 12/2003 | Stinson et al. |
| 2004/0052779 | A1 | 3/2004 | Stinson et al. |
| 2005/0074460 | A1 | 4/2005 | Lees et al. |
| 2005/0075486 | A1 | 4/2005 | Cassels et al. |
| 2005/0169941 | A1 | 8/2005 | Lees |
| 2005/0222434 | A1 | 10/2005 | Bessodes et al. |
| 2006/0165822 | A1 | 7/2006 | Lees |
| 2007/0065465 | A1 | 3/2007 | Lees |
| 2007/0292404 | A1 | 12/2007 | Lees |
| 2008/0019976 | A1 | 1/2008 | Lees |
| 2009/0081180 | A1 | 3/2009 | Lees |
| 2011/0263834 | A1 | 10/2011 | Lees et al. |
| 2012/0214187 | A1 | 8/2012 | Lees |
| 2013/0302877 | A1 | 11/2013 | Lees |

FOREIGN PATENT DOCUMENTS

| | | | | |
|---|---|---|---|---|
| JP | 2008510210 | 4/2008 | | |
| WO | WO 9521177 | 8/1995 | | |
| WO | WO 9521179 | 8/1995 | | |
| WO | WO96/17941 | 6/1996 | | |
| WO | WO 9617941 | 6/1996 | | |
| WO | WO 9617941 A2 | 6/1996 | ............. | C12N 15/62 |
| WO | WO 96/29094 | 9/1996 | | |
| WO | WO 9640662 | 12/1996 | | |
| WO | WO 0170685 | 9/2001 | | |
| WO | WO 0178787 | 10/2001 | | |
| WO | WO03/054511 | 7/2003 | | |
| WO | WO03/057849 | 7/2003 | | |
| WO | WO 03057849 | 7/2003 | | |
| WO | WO 03097699 | 11/2003 | | |
| WO | WO 2004104811 | 12/2004 | | |
| WO | WO 2005056608 | 6/2005 | | |
| WO | WO 2006032475 | 3/2006 | | |
| WO | WO2007/109129 | 9/2007 | | |
| WO | WO 2008021076 | 2/2008 | | |
| WO | WO 2011/05397 | 1/2011 | | |

OTHER PUBLICATIONS

Canadian Office Action for Application No. 2758323, dated Sep. 30, 2013.
PCT Patenbility Report for PCT/US13/45413, dated Dec. 2, 2013.
Webb, R.R., et al., "Synthesis of 1-(aminooxy)-4-A(3-nitro-2-pyridyl) dithiou butane and 1-(aminooxy)-4-A(3-nitro-2-pyridyl) dithiou but-2-ene, novel heterobifunctional cross-linking reagents," Bioconjugate Chemistry, ACS, Washington, DC, US, vol. 1, No. 2, p. 96-99 (1990).
Brask, J. et al., "Carbopetptides: chemoselective ligation of peptide aldehydes to an aminooxyfunctionalized D-galactose template," Journal of Peptide Science, vol. 6, p. 290-299 (2000).
Zeng, W. et al., "Assembly of synthetic peptide vaccines by chemoselective ligation of epitopes: influence of different chemical linkages and epitope orientations on biological activity," Vaccine, Butterworth Scientific, Guildford, GB, vol. 19, No. 28-29, p. 3843-3852 (Jul. 16, 2011).
Kubler-Kielb, J., et al., "A new method for conjugation of carbohydrates to proteins uing an aminoxy-thiol heterobifunctional linker," J. Org. Chem., vol. 70, p. 6987-6990 (Jul. 2005).
PCT Search Report for PCT/US2010/055107, dated Jul. 28, 2011.
PCT Patentability Report for PCT/US2010/055107, dated Jul. 28, 2011.
PCT Patentability Report for PCT/US2010/055107, dated May 8, 2012.
PCT Patentability Report for PCT/US2010/043387, dated Apr. 27, 2011.
Chinese Office Action for Chinese application No. 200580010225.4, dated May 18, 2012.
D. C. Watson, J. B. Robbins, and S. C. Szu, "Protection of mice against Salmonella typhimurium with an O-specific polysaccharide-protein conjugate vaccine," Infection and Immunity 60:4679-4686, 1992.
E. Konadu, J. Shiloach, D. A. Bryla, J. B. Robbins, and S. C. Szu, "Synthesis, characterization, and immunological properties in mice of conjugates composed of detoxified lipopolysaccharide of Salmonella paratyphi A bound to tetanus toxoid, with emphasis on the role of O-acetyls," Infect Immun. Jul. 1996; 64(7):2709-15.
Schneerson R, Barrera O, Sutton A, Robbins JB. Preparation, characterization, and immunogenicity of Haemophilus influenzae type b polysaccharide-protein conjugates. J Exp Med. Aug. 1, 1980;152(2):361-376.
PCT Search Report for PCT/US2010/043387, dated Apr. 27, 2011.
PCT Search Report for PCT/US10/61313, dated Feb. 15, 2011.
PCT Patentability Report for PCT/US10/61313, dated Feb. 15, 2011.
Chu, et al., "Further studies on the immunogenicity of Haemophilus influenzae type b and pneumococcal type 6A polysaccharide-protein conjugates," Inf. & Imm., 40:245-256 (1983).
Jennings, et al., "Conjugation of meningococcal lipopolysaccharide R-type oligosaccharides to tetanus toxoid as a route to a potential vaccine against group B Neisseria meningitides," Inf. & Immun., 43:407-412 (1984).
Laferriere et al., "The Synthesis of Streptococcus pnemoniae polysaccharide-tetanus toxoid conjugates and the effect of chain length on immunogenicity," Vaccine, 15:179 (1997).
Kohler, et al., "Continuous cultures of fused cells secreting antibody of predefined specificity," Nature, 256:495-7 (1975).
Morath, et al., "Structure-function relationship of cytokine induction by lipoteichoic acid from *Staphylococcus aureus*," J. Exp. Med. 193(3), p. 393-397 (2001).
PCT Search Report for PCT/US05/003040, dated Mar. 8, 2006.
Marcaurelle, L., et al., "Synthesis of oxime-linked mucin mimics containing tumor-related Tn and sialyl Tn antigens," Organic Letters, vol. 3, No. 23, p. 3691-3694 (2001).
Webb, R.R., et al., "Synthesis of 1-(aminooxy)-4-A(3-nitro-2-pyridyl) dithiou butane and 1- (aminooxy)-4-A(3-nitro-2-pyridyl) dithiou but-2-ene, novel heterobifunctional cross-linking reagents," Bioconjugate Chemistry, ACS, Washington, DC, US, vol. 1, No. 2, p. 96-99 (1990).
Brask, J. et al., "Carbopetptides: chemoselective ligation of peptide aldehydes to an aminooxy-functionalized D-galactose template," Journal of Peptide Science, vol. 6, p. 290-299 (2000).
Kubler-Kielb, J., et al., "A new method for conjugation of carbohydrates to proteins uing an aminooxy-thiol heterobiofunctional linker," J. Org. Chem., vol. 70, p. 6987-6990 (Jul. 2005).
PCT Patentability Report for PCT/US05/003040, dated Jul. 29, 2006.
EPO Exam Report for PCT/US05/003040, dated Feb. 22, 2008.
EPO Exam Report for PCT/US05/003040, dated Jul. 11, 2007.
AU Exam Report for PCT/US05/003040, dated Mar. 4, 2011.
JP Exam Report for PCT/US05/003040, dated May 19, 2011.
Renaudet & Dumy, "Chemoselectively template-assembled glycopeptides presenting clustered cancer related t-antigen," Tetrahedron Letters, vol. 45, No. 1, p. 65-68 (Jan. 2004).
JP Exam Report for PCT/US05/003040, dated Nov. 22, 2010.
Chinese Exam Report for PCT/US05/003040, dated Oct. 24, 2011.
Chinese Exam Report for PCT/US05/003040, dated Apr. 3, 2009.
CA Exam Report for PCT/US05/003040, dated Jun. 11, 2010.
CA Exam Report for PCT/US05/003040, dated Jul. 13, 2009.
AU Exam Report for PCT/US05/003040, dated Sep. 14, 2007.
India Exam Report for PCT/US05/003040, dated Sep. 14, 2007.
PCT Patentability Report for PCT/US2010/061133, dated Jun. 19, 2012.
Arkivoc, 2007(iii), pp. 5-12.
Tetraheddron, 2005, 61, pp. 5889-5894.
Korean Office Action for Application No. 10-2014-7007579, dated Oct. 15, 2014.
EP Search Report for PCT/US2010/061133, dated Sep. 7, 2015.
Zuber, et al., "Enhanced ligation of DNA with a synthetic effector molecule," Journal of the American Chemical Society, vol. 115, No. 11, pp. 4939-4940, Jan. 1, 1993.
Kim, et al, "2-Cyanopyridazin-3(2H)-ones: effective and chemoselective electrophilic cyanating agents," Tetradedron 61, pp. 5889-5894, May 10, 2005.

ACTIVATION OF POLYSACCHARIDES VIA THE CYANYLATING AGENT, 1-CYANOIMIDAZOLE (1-CI), IN THE PREPARATION OF POLYSACCHARIDE/PROTEIN CONJUGATE VACCINES

REFERENCE TO RELATED APPLICATIONS

This application is a continuation of and claims priority to U.S. application Ser. No. 13/514,356 filed Jun. 7, 2012, which is a national stage submission of International Application No. PCT/US2010/061133 filed Dec. 17, 2010, which claims priority to U.S. Provisional Application No. 61/287,593 filed Dec. 17, 2009, and the entirety of each is hereby incorporated by reference.

BACKGROUND

1. Field of Invention This invention is directed to reagents and methods of conjugating proteins to carbohydrates and, in particular, the processes and chemicals used in the manufacture of vaccines, and also the vaccines manufactured by the process.
2. Description of the Background Vaccines that contain protein covalently linked to carbohydrate have proven remarkably successful in inducing an immune response to the carbohydrate moiety. Examples of such vaccines, known as "conjugates" are available for Haemophilus influenzae type b (e.g., ActHib, Hiberix), *Neisseria meningiditis* types A C W and Y (e.g., Menactra) and *S. pneumoniae* (e.g., Prevnar, Synflorix). In order for the protein to be linked to the carbohydrate, the latter generally needs to be activated so that it can be reacted with the protein, either directly or via a spacer (Dick, W. E. Jr and Beurret, M. Glyconjugates of bacterial carbohydrate antigens. A survey and consideration of design and preparation factors. In: Conjugate Vaccines (Eds Cruse, J. M. and Lewis, R. E.). Karger, Basel, 1989. One means of activation is through oxidation of the carbohydrate to produce aldehydes, which are then linked to lysines on protein through reductive amination. In other cases, the protein is first functionalized with hydrazides or aminooxy groups, which are subsequently reacted with aldehydes on the carbohydrate (Lees, A. Use of amino-oxy functional groups in the preparation of protein-polysaccharide (PS) conjugate vaccines United States Patent Publication No. 2005/0169941; which is incorporated by reference). Another method for activating polysaccharides is with the use of cyanogen bromide, to form a cyano-ester on the polysaccharide which is subsequently reacted with a spacer molecule such as adipic dihydrazide. The functionalized polysaccharide is then reacted with the protein. Improved methods for cyanating polysaccharides use 1-cyano-4-dimethylaminopyridine tetrafluoroborate (CDAP) (Lees, A., Producing immunogenic constructs using soluble carbohydrates activated via organic cyanylating reagents. U.S. Pat. Nos. 5,651,971; 5,693,326; and 5,849,301). CDAP allows for protein to be linked directly to the polysaccharide. CDAP can also be used to functionalize the polysaccharide with a spacer, which is subsequently linked to the protein. Hydrazide or aminooxy functionalized proteins can also be linked to CDAP activated polysaccharides (U.S. Pat. No. 5,849,301; which is incorporated by reference).

SUMMARY OF THE INVENTION

The present invention, overcomes the problems and disadvantages associated with current strategies and designs in the manufacture of vaccines, and provides new tools and methods of protein conjugation especially for vaccine manufacture. One embodiment of the invention is directed to a process of conjugation of a carbohydrate comprising: mixing a compound such as 1-CBT, or 1-CI, or CPPT, or 2-CPO, or a functional derivative or modification thereof with the chemical compound to create an activated chemical compound; and mixing the activated compound with a second compound to create a conjugate. Preferably the chemical compound is a natural or synthetic carbohydrate, polysaccharide, oligosaccharide, or combination thereof. Also preferably, the second compound is a peptide, a polypeptide or a protein, which may be an antigenic molecule. Conjugation may be direct or indirect with the additional of functional groups that facilitate conjugation. The process preferably further comprises removing components with a lower molecular weight than the conjugate for example, by dialysis filtration, chromatography, or a combination thereof. The resulting conjugate is preferably a vaccine or a diagnostic agent. The process may further comprise including a linking compound between the activated compound and the second compound. Preferably the steps of the process, as well as the inclusion of a linker, are performed together, but each may be performed independently.

Another embodiment of the invention is directed to a vaccine produced by the processes of the invention. Preferably the vaccine further comprises a pharmaceutically acceptable carrier which may include, but is not limited to water, saline, alcohol, saccharides, polysaccharides, oil, or combinations thereof.

Other embodiments and advantages of the invention are set forth in part in the description, which follows, and in part, may be obvious from this description, or may be learned from the practice of the invention.

DESCRIPTION OF THE INVENTION

Figure 1:
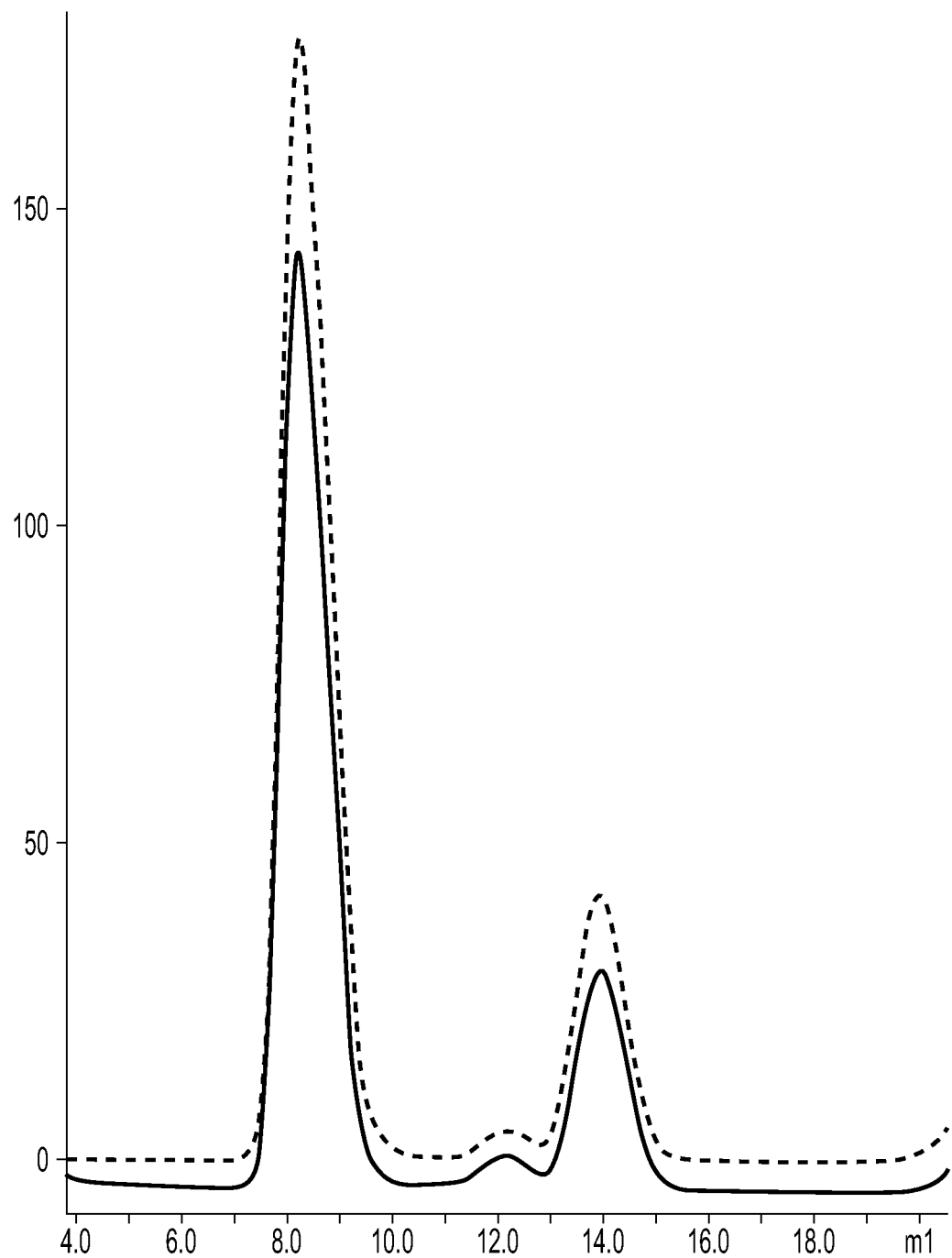
FIG. 1. Overlaid chromatogram of BSA/CDAP/dextran and BSA/CPPT/dextran run on a Superdex200 column (1×30cm) gel filtration column.

One embodiment of the invention is directed to a process of conjugation of a chemical compound comprising mixing CPPT, 1-CBT, 1-CI, or 2-CPO, or a functional derivative or conservative modification of any of the preceding compounds, with the chemical compound to create an activated chemical compound. The activated compound is mixed with a second compound to create a conjugate. These steps may be performed independently or together, and may include another compound as a linker between the two. Preferably the activated compound is mixed with a linker molecule which is subsequently reacted with a second compound to create a conjugate. Preferred linkers include but are not limited to hexanediamine, ethylenediamine, hydrazine, adipic dihydrazide, or 1,6-diaminooxyhexane.

Conjugation may be direct or indirect, meaning with or without the addition of functional groups that facilitate conjugation. Preferably, the chemical compound is a natural or synthetic carbohydrate, polysaccharide, oligosaccharide, or combination thereof. Preferably the second compound is a peptide, a polypeptide or a protein, and more preferably the second compound is an antigenic molecule for the preparation of a vaccine of as a diagnostic reagent.

This invention provides novel reagents for cyanating polysaccharides in aqueous or part aqueous solutions so that they may be covalently linked to proteins either directly or through a spacer. The examples illustrate the use of these reagents with a variety of polysaccharides and proteins showing that the methods are generally applicable.

Carbohydrate, polysaccharide and oligosaccharide are used interchangeably in this application. The method can employ either natural or synthetic carbohydrate.

Protein can refer to natural, recombinant or synthetic material. It can include peptides. Other molecules besides protein can be used as the second moiety to link either directly or indirectly to the activated carbohydrate.

Direct conjugation refers to linking of the protein to the activated carbohydrate without introducing additional functional groups. Indirect conjugation refers to the addition of functional groups which are used to facilitate conjugation. For example, carbohydrate can be functionalized with amines which are subsequently reacted with bromoacetyl groups. The bromoacetylated carbohydrate is then reacted with thiolated protein. (Hermanson, GT, Bioconjugate Techniques, Academic Press, $2^{nd}$ ed, 2008). The term "functionalization" generally means to chemically attach a group to add functionality, for example, to facilitate conjugation. Examples include functionalization of proteins with hydrazides or aminooxy groups and functionalization of carbohydrate with amino groups.

Methods and Reagents

Conjugation of the protein to the carbohydrate increases its molecular weight, which can be monitored using analytical size exclusion chromatography (SEC HPLC). The earlier the material elutes the higher the molecular weight, and protein is generally monitored by its absorbance at 280 nm. Thus the shift of absorbance to an earlier time is an indication of an increase in molecular weight and hence of conjugation. A BioSep G4000 SEC column (Phenomenex) or similar column was used for SEC HPLC in a Waters 600 system equipped with Empower software. Amines and hydrazides were assayed using TNBS as generally described in: "Spectrophotometric determination of hydrazine, hydrazides, and their mixtures with trinitrobenzenesulfonic acid" Qi XY, Keyhani N O, Lee Y C. Anal Biochem. 1988 Nov 15;175(1):139-44 (incorporated by reference) and Vidal and Franci, J Immun. Meth 86:155, 1986.

Protein concentration was determined from its extinction coefficient and absorbance at 280 nm. Carbohydrate was assayed by the method of Monsigny M. et al. (*Anal Biochem.* 175(2):525-30, 1988; incorporated by reference).

Figure 5:
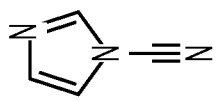
FIG. 5. Chemical structures of CPPT (1-cyano-4-pyrrolidinopyridinium tetrafluorborate; also referred to as CPIP), 1-CBT (1-cyanobenzotriazole), 1-CI (1-cyanoimidazole), and 2-CPO (2-cyanopyridazine-3(2H)one).
Figure 5:
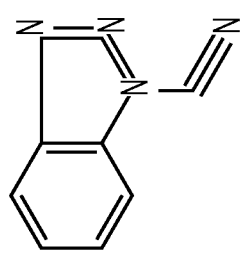
Figure 5:
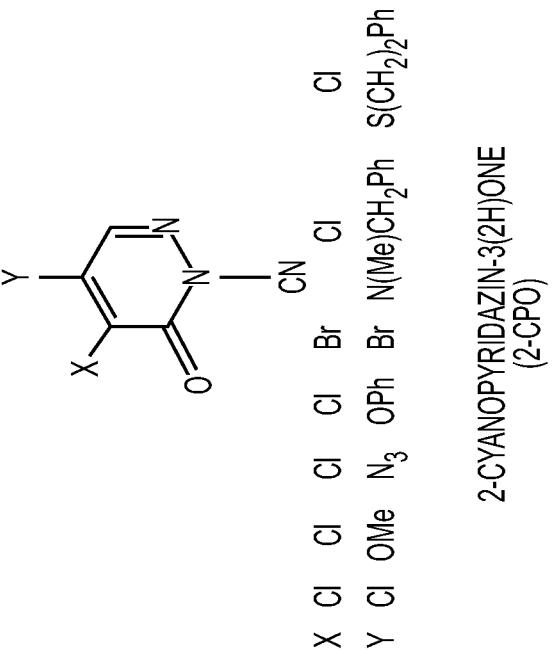

1-cyano-4-pyrrolidinopyridinium tetrafluoroborate (CPPT) was prepared by Wilmington PharmaTech, Lot No. 1795-1536-10 and was greater than 97% pure as determined by reverse phase HPLC (see FIG. 5). 1-cyano-4-dimethylaminopyridine tetrafluoroborate (CDAP) was provided from Merck Kga. 1-cyano-imidazole (1-CI) was purchased from Apin Chemicals (Abingdon, UK) (see FIG. 5). 1-cyano-benzenetriazole (1-CBT) was purchased from Sigma Aldrich (see FIG. 5). CRM and tetanus toxoid were provided from the Serum Institute of India (Pune). BSA was purchased from Amresco (Solon, Ohio). Pneumococcal polysaccharides were obtained from the Serum Institute of India or the ATCC (Manassas, Va.). Hib PRP and Neisseria meningitidis polysaccharides were obtained from the Serum Institute of India. T2000 dextran (GE Healthcare) was fractionated using an S400HR gel filtration column (GE Healthcare) to prepare a high molecular weight fraction. Other reagents used include: N-Methyl-2-pyrrolidone (NMP), hexanediamine.2HCl, and triethylamine (TEA) were from Sigma-Aldrich. Acetonitrile was from GFS Chemical.

The following examples illustrate embodiments of the invention, but should not be viewed as limiting the scope of the invention.

EXAMPLE 1

Model System

As a Model System, BSA was covalently linked to the polysaccharide dextran, either directly or through a spacer.

CDAP and CPPT were each brought to 0.43 M in acetonitrile and 120 ul added to 2 ml of dextran (6 mg/ml in saline+ 0.02% sodium azide). After 30 sec, triethylamine was added to each (~7u1) to maintain the pH at about pH 9.8. At 2 min, 1 ml aliquots of the activated dextran was removed ad added to either 1 ml of a 0.5 M solution of hexane diamine or to a solution of 1 ml of BSA (10 mg/ml). After 4 hours, the hexanediamine derivatized dextran solutions were dialyzed overnight into saline with frequent changes. To further remove low molecular weight reagents, the solutions were each brought to ~6 ml, concentrated using a Corning spin filter device (Spin-X 10 kDa cutoff) and the process repeated. The filtrate from the second spin was assayed using trinitrobenzesulfonic acid (TNBS) and found to be essentially negative for amines. The desalted retentate was assayed for amines and dextran. The BSA-dextran conjugates were incubated overnight at 4° C. and then fractionated on a Superdex200 size exclusion column (GE Healthcare), equilibrated with PBS. The elution profile for the two conjugates is shown in FIG. 1. The void volume peak was pooled and assayed for BSA and dextran (see Table 1).

TABLE 1

| Activator | mg BSA/mg Dex | $NH_2$/100 kDa Dex |
|---|---|---|
| CDAP | 0.71 | 59 |
| CPPT | 0.90 | 78 |

This data shows that CPPT activates dextran as well as CDAP and possibly better. It demonstrates that protein can be directly conjugated to CPPT activated polysaccharide.

EXAMPLE 2

Functionalization of Polysaccharides With Amines Using CPPT

Solutions of 7.5 mg/ml of Haemophilus influenza (Hib), Neisseria meningitidis A (MenA) and Neisseria meningitidis C (MenC) capsular polysaccharides was prepared. To 1.35 ml of each, 75 ul of 100 mg/ml CPPT in acetonitrile was added. At 30 sec, 5 ul of TEA was added to the Hib and MenA polysaccharides. 6 ul of TEA was added to the MenC solution. At 2.5 min, 0.6 ml of the activated PS was added to 0.6 ml of 0.5 M hexanediamine. After 3 hr, each was dialyzed extensively against saline.

Each solution was assayed for polysaccharide using the resorcinol sulfuric acid assay with the corresponding polysaccharide as the standard for MenA and MenC. Ribose was used as the standard for the Hib polysaccharide, with 1 mole ribose per repeat unit and a repeat unit MW of 243 g/mole (see Table 2).

TABLE 2

| Polysaccharide | NH2/100 kDa |
| --- | --- |
| Hib | 38 |
| Mena | 19.5 |
| MenC | 13 |

This table further illustrates the use of CPPT to functionalize a variety of polysaccharides.

EXAMPLE 3

Derivatization of Dextran, a Model Polysaccharide, Using 1-Cyano-Imidazole 30 mg of 1-CI was added to 2 ml of 20 mg/ml solution of T2000 dextran (GE Healthcare). Five 100 ul aliquots of 0.2 M triethylamine were added to maintain the pH at 9-9.2. After about three minutes, 2 ml of 0.5 M hexanediamine was added and the pH adjusted to 9 with 0.5 M NaOH. After 2 hr of reaction, the solution was dialyzed exhaustively into saline. The solution was clarified by centrifugation and assayed for dextran and amines. The product was found to contain 27 amines/100 kDa of dextran, showing that 1-CI can be used to functionalize polysaccharides with amines.

EXAMPLE 4

Direct Conjugation of a Model Protein to a Model PS Using 1-CI (BSA-Dextran)

A solution of 13.5 mg/ml of high molecular weight dextran was prepared. 67.5 ul of a 100 mg/ml solution of 1-CI in NMP was added to 1 ml and 30 sec later, 4 aliquots of 100 ul each of 0.2 M TEA added, followed by about 20 ul of 0.5 M NaOH. At about 3.5 min, 0.5 ml of a 20 mg/ml solution of BSA was added. The pH was raised to about 8.5 by the addition of 2 aliquots of 100 ul each 0.1 M sodium borate, pH 9.0. After two days at 4° C., the reaction mixture was analyzed by SEC HPLC. The figure shows that the BSA+1-CI activated dextran now elutes much earlier from the size exclusion column, indicating higher molecular weight due to conjugation to the polysaccharide.

EXAMPLE 5

Activation of Other PS with 1-CI

Capsular polysaccharides from pneumococcal serotypes 1 PS (Ps1) and 6B PS (Ps6B) were prepared at 10 mg/ml in saline +0.02% sodium azide. 9.3 mg of 1-CI suspended in 93 ul NMP was added to 1 ml of Psi followed by 8 100 ul aliquots of 0.2 M TEA. At 2.5 min, 0.5 ml of 1 M hexanediamine was added, followed by 2 aliquots of 100 ul each of 0.5 M NaOH. The pH was approximately 9. 100 ul of a 100 mg/ml solution of 1-CI in NMP was added to 1 ml of the Ps6B solution. Two 100 ul aliquots of 0.2 M TEA were added, followed by 2 aliquots of 50 ul each of 0.5 M NaOH to maintain the pH at ~9.5-10.8. At 2.5 min, 0.5 ml of 1 M hexanediamine was added along with 50 ul of 0.5 M NaOH. After about 3 hours, each was dialyzed extensively against saline. Each was then assayed for polysaccharide using the resorcinol sulfuric acid assay and for amines using TNBS (see Table 3).

TABLE 3

| | Amines/100 kDa PS |
| --- | --- |
| Ps1-NH$_2$ | 9.8 |
| Ps6B-NH$_2$ | 4.5 |

Thus it is clear that 1-CI can be used to activate and functionalize polysaccharides.

EXAMPLE 6

Indirect Conjugation to Polysaccharide Functionalized Using 1-CI 239 ul of 1 M HEPES, pH 8 was added to a solution of about 9.5 mg in 2.2 ml of the Ps6B-NH$_2$ prepared in Example 5. 170 ul of 0.1 M NHS bromoacetate in NMP was added. After 1 hr, the solution was desalted by repeated washes using an Amicon Ultra15 30 kDa cutoff spin filter, using 10 mM NaPO$_4$+5mM EDTA pH 6.8 buffer. The retentate was then brought to a final volume of about 0.7 ml. Tetanus toxoid was thiolated as follows: 571 ul of tetanus toxoid (35 mg/ml) was brought to pH 8 by the addition of 64 ul 1 M HEPES. 27 ul of 0.1 M SPDP in NMP was slowly added. After about 2 hrs, the pH was reduced to 5.7 and 33 ul of 0.5 M DTT added to deprotect the thiol. After 30 min, the solution was desalted on a 1×15cm G25 column, equilibrated with 10 mM NaPO$_4$+ 5mM EDTA pH 6.8 buffer. The void volume was pooled & concentrated to a final concentration of about 62 mg/ml. The thiol content was determined using DTNB. The tetanus had a ratio of about 6 mole thiols/mole TT. The bromoacetylated polysaccharide and thiolated TT were combined as follows: 0.66 ml Ps6B-BrAc+73 ul 1 M HEPES, pH 8+230 ul thiolated TT.

Figure 2:
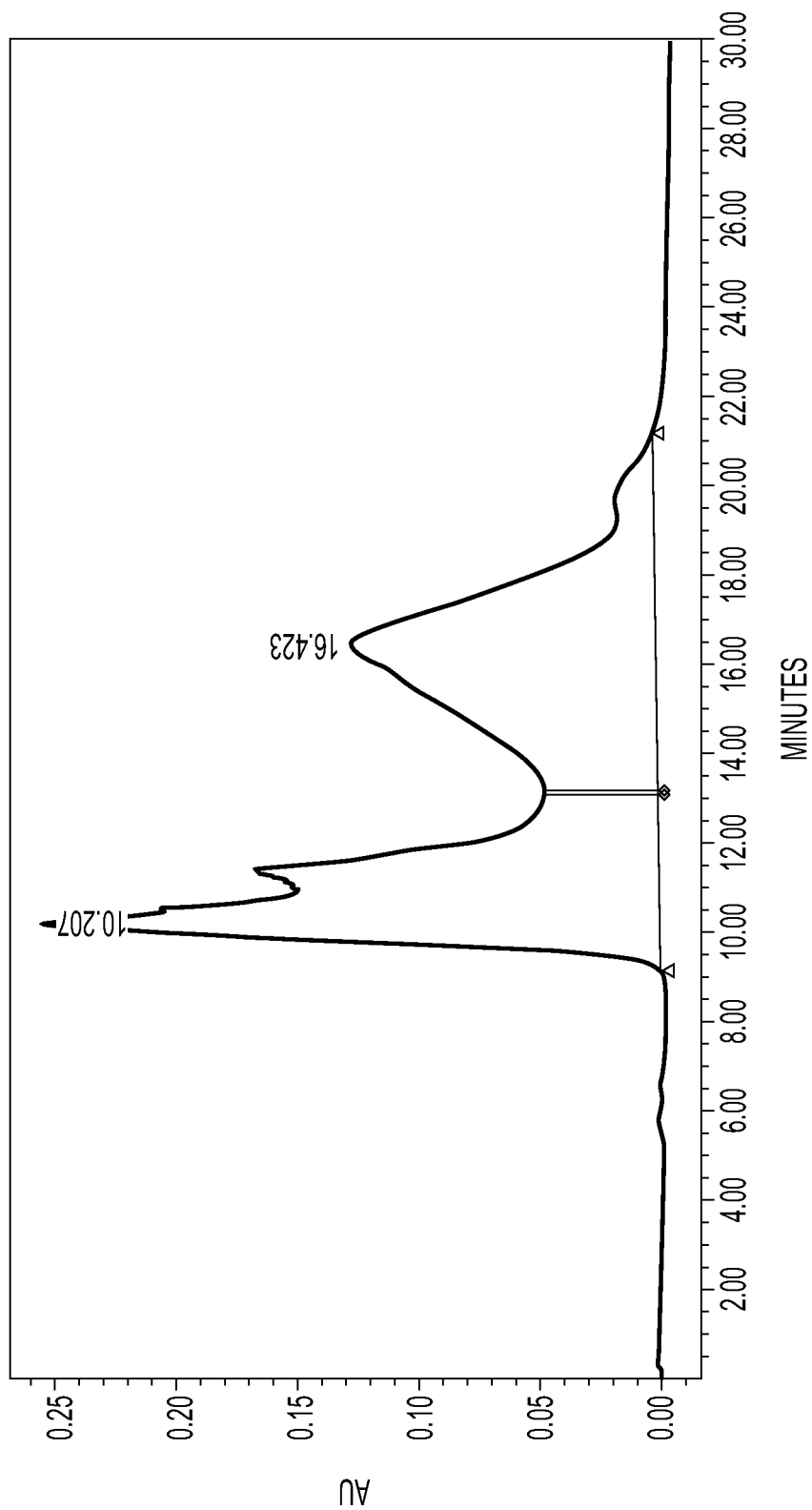
FIG. 2. SEC HPLC analysis of indirect conjugation to polysaccharide functionalized using 1-CI.

The reaction was allowed to proceed overnight at 4° C. and then analyzed by SEC HPLC (FIG. 2). The conjugate was fractionated by gel filtration on an S400HR column size exclusion (GE Healthcare). The void volume fractions, containing the high molecular weight material, were pooled and assayed for protein and carbohydrate. The conjugate was found to have about 1 mg TT per mg Ps6. This indicates that 1-CI can be used for the indirect conjugation of proteins to carbohydrate.

EXAMPLE 7

Direct Conjugation of a Protein to Polysaccharide Using 1-CI

Figure 3:
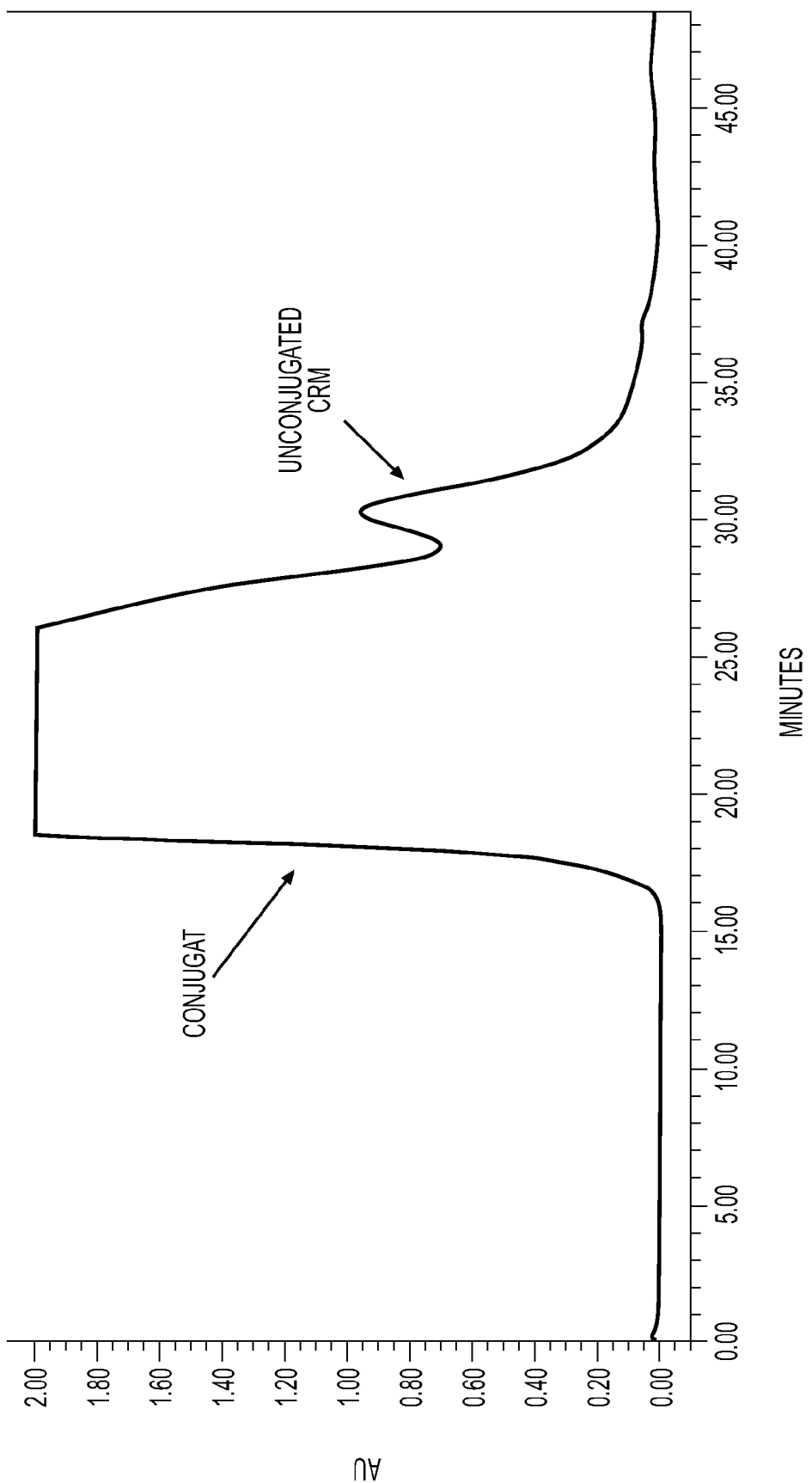
FIG. 3. Chromatogram of CRM(1-CI/Ps6A) conjugate on Superdex200.
Figure 4:
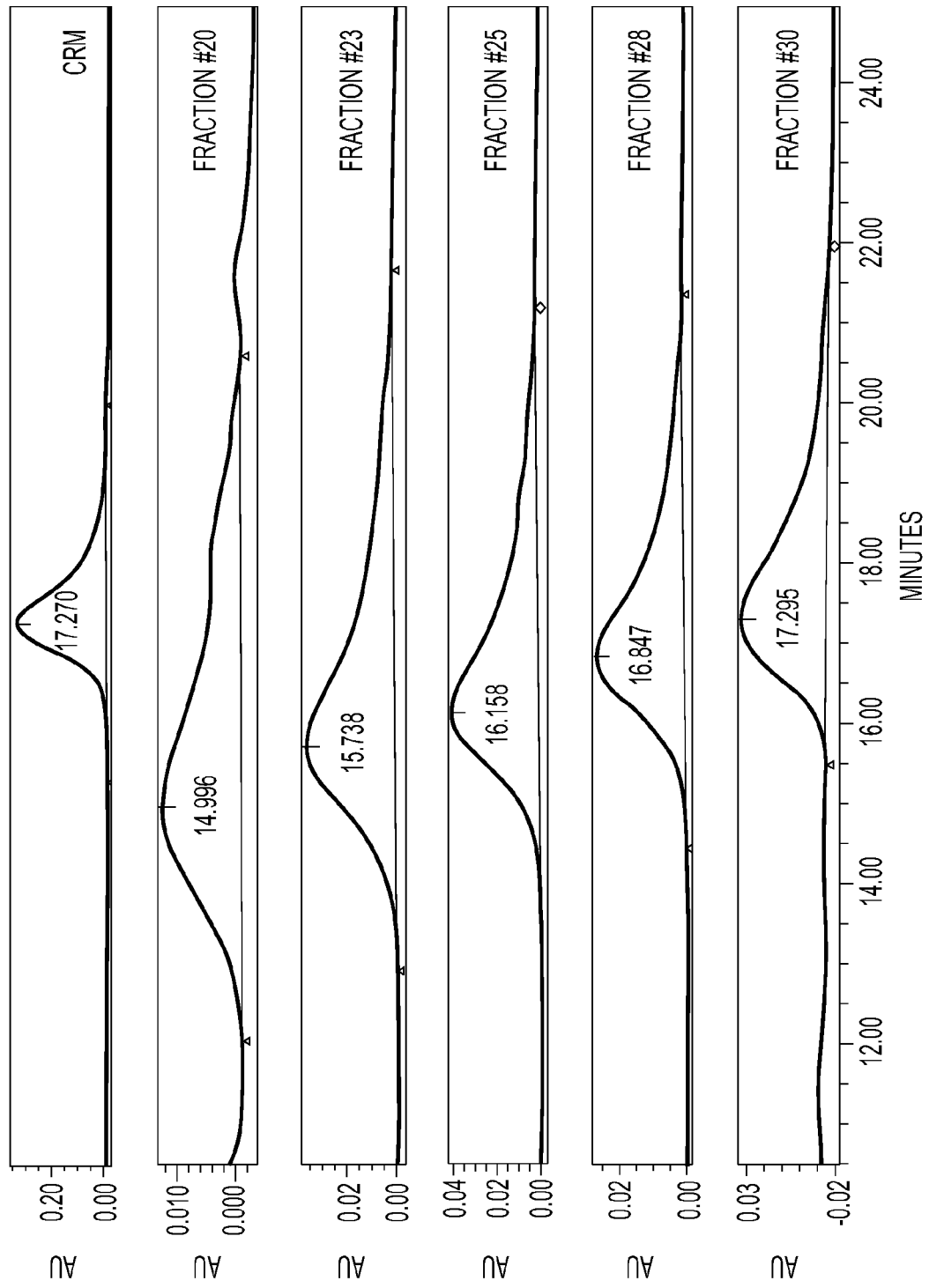
FIG. 4. SEC HPLC analysis of Superdex 200 fractions.

Capsular polysaccharide from pnueumococcal serotype 6A (Ps6A) was solubilized in water at 10 mg/ml. Each of 5 1 ml tubes was heated to 80° C. for 2 min and 1 ml 0.1 M sodium borate, pH 9 added to each. After 2.5 hr, the tubes were cooled on ice and then dialyzed. 25 ul of TEA was added to 10 ml of the hydrolyzed Ps6A at 5 mg/ml and 50 mg of 1-CI added while vortexing. At 2.5 min, 30 ml of CRM at 17.2 mg/ml was added and the pH maintained at about 9. After an overnight reaction, the solution was concentrated to about 1 ml using an Amicon Ultra 15 30 kDa cutoff spin device. 0.5 ml was loaded onto a Superdex 200 column (1×30cm), equilibrated with 10 mM sodium borate, 150 mM NaCl, pH 9 and the column run at 0.5 ml/min. The chromatogram is shown in FIG. 3. 0.5 ml fractions were collected and selective fractions analyzed by SEC HPLC. The SEC chromatograms are shown in FIG. 4 and indicate that all the Fractions are higher MW than the unconjugated CRM. As shown, Fractions 20-28 all elute earlier than unconjugated CRM, indicating that each is of a higher molecular weight.

EXAMPLE 8

Functionalization of a Polysaccharide with 1-Cyanobenzotrazole (1-CBT)

12 mg of 1-CBT were suspended in 240 ul of acetonitrile+120 ul of NMP. 120 ul of 0.2 M were added to 0.5 ml of 20mg/ml T2000 dextran (10 mg) followed by the addition of 120 ul of the 1-CBT suspension. At about 3 min, 0.5 ml of 0.5 M adipic dihydrazide was added. After 2 hrs of reaction, the solution was dialyzed extensively against saline over 2 days. The solution was then centrifuged and assayed for dextran and hydrazides.

Approximately 9.5 mg of dextran was recovered with a ratio of about 11 hydrazides per 100 kDa of dextran. To confirm that the hydrazides were linked to the dextran, an aliquot of TNBS labeled hydrazide-dextran was examined by SEC HPLC with monitoring at 500 nm, where the TNBS-hydrazide adduct adsorbs. The chromatogram indicated that the trinitrobenzene was associated with the high molecular weight dextran, showing that the hydrazide was indeed linked to the dextran. This shows that 1-CBT can be used to functionalize polysaccharides.

EXAMPLE 9

Direct Conjugation of Protein to 1-CBT Activated Polysaccharide 120 ul of 0.2 M TEA was added to 500 ul of a 20 mg/ml solution of T2000 dextran and 160 ul of a 50 mg/ml suspension of 1-CBT in acetonitrile added. At about 2 min, 200 ul of a 47 mg/ml solution of BSA in saline was added and the solution became more viscous. After an overnight reaction, the conjugate was analyzed by SEC HPLC. The majority of the BSA eluted at the void volume of the column, indicating that it was high molecular weight. This demonstrates that 1-CBT can be used to directly conjugate proteins to polysaccharides.

EXAMPLE 10

A selected 2-Cyanopyridazin-3(2H)-ones (See Kim et al, Tetrahedron 61:5889, 2005) is Synthesized as Described in Kim et al., to Cyanate Carbohydrate.

The carbohydrate is activated using 2-CPO (X=Cl, Y=Cl) and is then directly reacted with a protein or functionalized, e.g., with amino groups. Reagent 2a (See Scheme 1 Kim et al.) is made up at 100 mg/ml in acetonitrile and added to a 10 mg/ml solution of pneumococcal type 14 polysaccharide (Ps14) at ratio of 1 mg reagent to 1 mg carbohydrate. The pH is raised to pH 9.5 using triethylamine and maintained. After 2.5 min, half the solution is added to an equal volume of 0.5 M hexanediamine and the pH adjusted to about 8. The other half of the solution is combined with an equal weight of tetanus toxoid in 10 mg/ml solution. After an overnight incubation at 4° C., the hexanediamine polysaccharide solution is extensively dialyzed against saline and then assayed for amines and polysaccharide. A ratio of 10 amines per 100 kDa polysaccharide is found. The tetanus polysaccharide solution is fractionated on a S400HR column (GE Healthcare) to remove unconjugated protein. The protein and polysaccharide concentrations are determined. A ratio of about 0.75 mg protein per mg polysaccharide is found.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A process of conjugation of a carbohydrate comprising:
   mixing 1-cyanoimidazole (1-CI) with the carbohydrate to create an activated chemical compound; and
   mixing the activated compound with an antigenic second compound to create a conjugate, wherein the second compound is a peptide, a polypeptide or a protein.

2. The process of claim 1, wherein the carbohydrate is a natural or synthetic carbohydrate, polysaccharide, oligosaccharide, or combination thereof.

3. The process of claim 1, wherein conjugation is direct or indirect with the addition of functional groups that facilitate conjugation.

4. The process of claim 1, further comprising removing components with a lower molecular weight than the conjugate by dialysis, filtration, chromatography, or a combination thereof.

5. The process of claim 1, wherein the conjugate is a vaccine or a diagnostic agent.

6. The process of claim 1, wherein the steps are performed together.

7. The process of claim 1, further comprising mixing the activated compound with hexanediamine, ethylenediamine, hydrazine, adipic dihydrazide, or 1,6-diaminooxyhexane to form a linking group between the activated compound and the antigenic second compound.

8. A vaccine or diagnostic agent produced by the process of claim 1.

* * * * *